United States Patent [19]

Chopra et al.

[11] Patent Number: 5,342,627
[45] Date of Patent: Aug. 30, 1994

[54] CONTROLLED RELEASE DEVICE

[75] Inventors: Sham K. Chopra; Avinash K. Nangia; David Lee; Thomas P. Molloy, all of Mississauga, Canada

[73] Assignee: Glaxo Canada Inc., Mississauga, Canada

[21] Appl. No.: 975,079

[22] Filed: Nov. 12, 1992

[30] Foreign Application Priority Data

Nov. 13, 1991 [GB] United Kingdom ............ 9124106
Nov. 13, 1991 [GB] United Kingdom ............ 9124108
Mar. 12, 1992 [GB] United Kingdom ............ 9205463

[51] Int. Cl.$^5$ .................. A61K 9/22; A61K 9/28
[52] U.S. Cl. .................. 424/473; 424/438; 424/468; 424/469; 424/470; 424/471; 424/474; 424/480; 424/482; 424/484
[58] Field of Search ............ 424/438, 468, 471, 473, 424/474, 484, 482

*Primary Examiner*—Thurman K. Page
*Assistant Examiner*—James M. Spear
*Attorney, Agent, or Firm*—Bacon & Thomas

[57] ABSTRACT

The invention relates to a device for the release of at least one active substance (e.g. ranitidine) into a fluid medium by dissolution comprising a covering, which is impermeable to the active substance and the fluid, having at least one aperture therein and defining a shaped cavity, the cavity being filled by a shaped core comprising the active substance, and wherein: on exposure of the device to the fluid medium, a surface of the core is exposed and dissolution of the surface by the fluid medium causes a change in at least one dimension of the area of the surface, while the surface area of the exposed surface remains substantially constant over at least 50% of the total dissolution time of the core; or the active substance is disposed in a matrix of an inert insoluble excipient, the device being axially symmetrical, with its aperture being peripherally disposed so that the release surface of core which is exposed through the aperture is substantially cylindrical or part of a cylinder in shape; whereby to allow substantially constant release of the active substance over at least part of the dissolution time; and processes for its preparation.

15 Claims, 8 Drawing Sheets

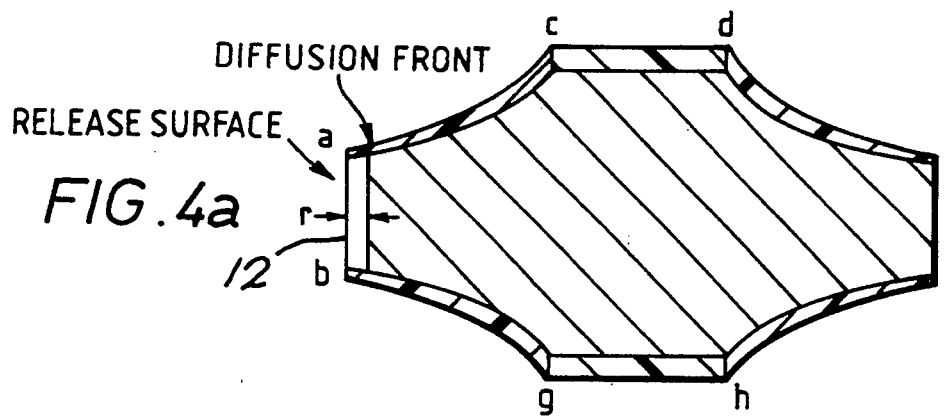
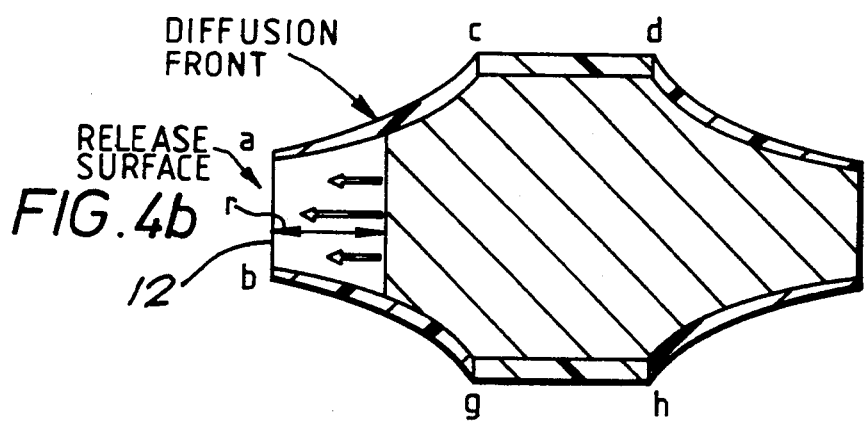
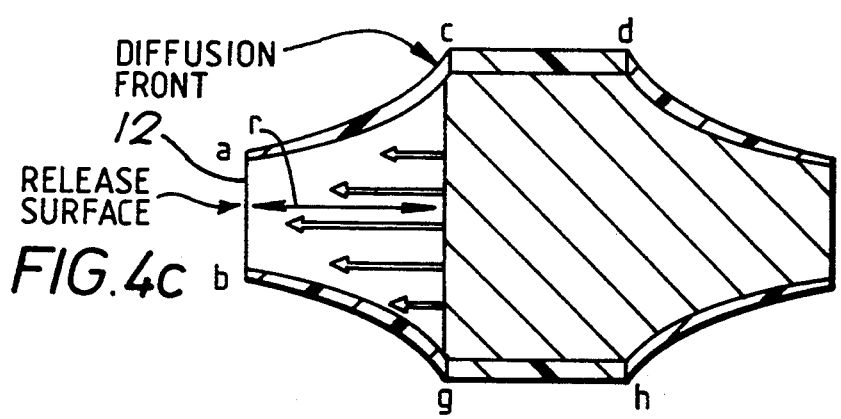

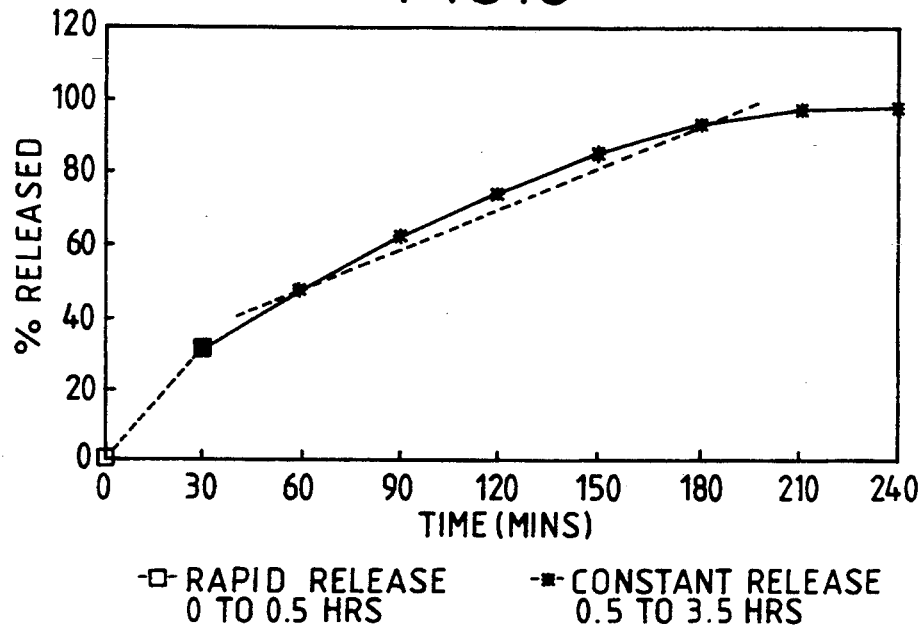
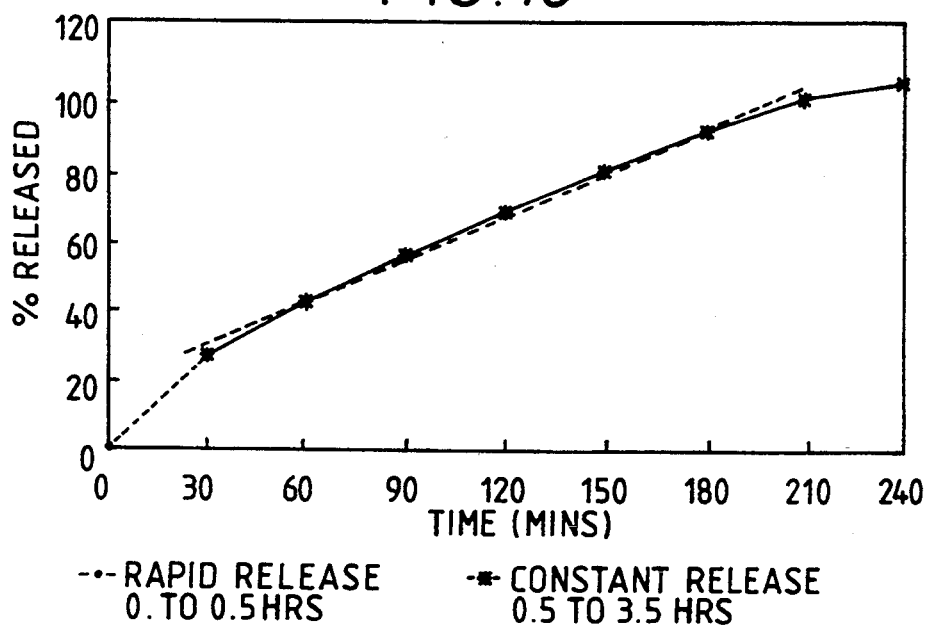

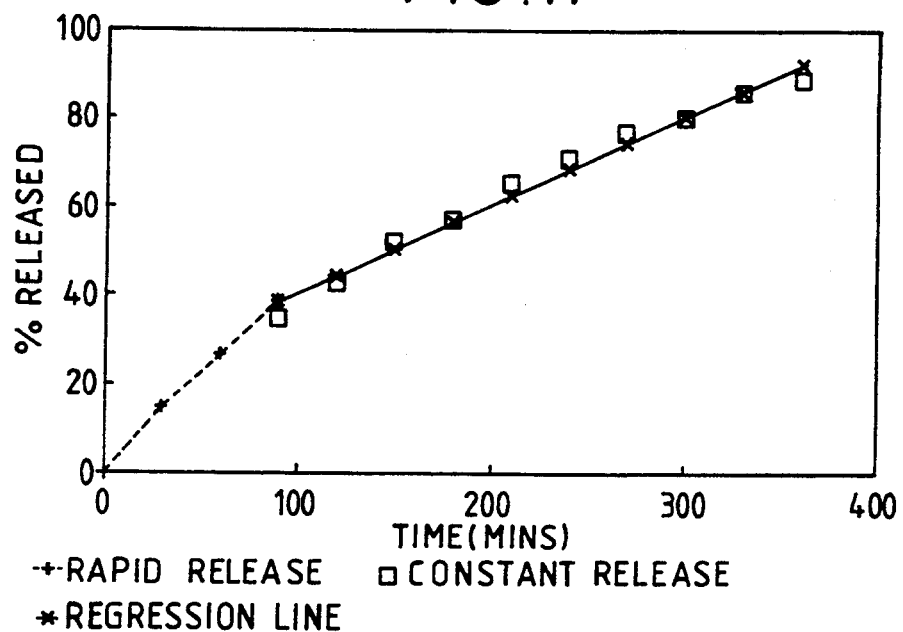
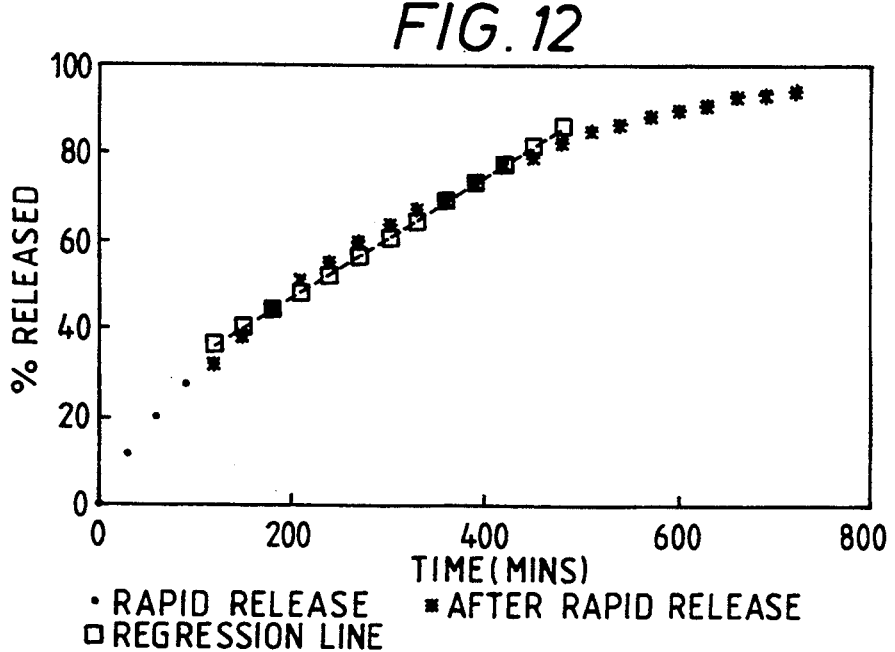

CONTROLLED RELEASE DEVICE

The present invention relates to a device for the controlled release of an active substance, for example an $H_2$-antagonist such as ranitidine. In particular it relates to a tablet whose geometrical configuration and formulation is such that it releases active substance at a constant rate over a significant portion of the total dissolution time.

Ranitidine, N-[2-[[[5-(dimethylamino)methyl-2-furanyl]methyl]thio]ethyl]-N'-methyl-2-nitro-1,1-ethenediamine, and its pharmaceutically acceptable salts are described in British Patent Specification No. 1565966, and a particular crystalline form of ranitidine hydrochloride is described and claimed in GB-B-2084580. In both of these specifications there is reference to a variety of formulations including preparations for oral, topical, parenteral or rectal administration. Oral preparations of ranitidine are further described in GB-B-2142820, GB-B-2198352, GB-B-2218336, GB-B-2219940, GB-B2222772 and GB-A-2229094.

Ranitidine is a potent histamine $H_2$-antagonist which, in the form of its hydrochloride salt, is widely used in the treatment of conditions where there is an advantage in lowering gastric acidity. Such conditions include duodenal and gastric ulceration, reflux oesophagitis and Zollinger-Ellison syndrome. Ranitidine may also be used prophylactically in surgical procedures, and in the treatment of allergic and inflammatory conditions where histamine is a known mediator.

Throughout this specification the term "ranitidine" is intended to include ranitidine and pharmaceutically acceptable salts thereof, preferably the hydrochloride salt thereof.

There are currently available many delayed release and controlled release formulations for dispensing an active substance. This is particularly true in respect of pharmaceuticals, although such formulations are used in other areas such as pesticides, swimming pool disinfectants, etc.

It is known that to obtain a constant drug level in the blood, a regulated drug delivery system should release the drug at a constant rate. Attempts have been made to achieve this by controlling the geometry of uncoated tablets of active substance. Thus, for example, U.S. Pat. No. 3113076 describes an uncoated tablet having inner and outer surfaces of active substance which are dissolved in an attempt to maintain a constant surface area. However, in use, such an uncoated, exposed system does not provide a reliable controlled release formulation.

Controlled-release systems are also known which include a core of active substance and inert excipients surrounded by a porous, microporous or semipermeable polymeric membrane. These systems release drug at a constant rate as long as the concentration of the osmotic agent, in osmotic systems coated with semipermeable membranes, and the concentration of the drug, in diffusion systems of reservoir type coated with microporous or porous membranes is above the saturation point. However, once the concentration falls below the saturation point, the release rate decreases parabolically towards zero.

Controlled release systems are known which include an insoluble coating surrounding an active substance disposed in an insoluble matrix which is exposed via a small aperture. The basis for such systems is that the surface area of exposed active substance continuously increases, as dissolution proceeds, in compensation for the increased diffusion path between the aperture and the dissolving surface of active substance in the inert matrix. The rate-determining factor is the diffusion path length. Thus, EP-A-259219 describes a ring-shaped system in which the aperture is present at the centre of the ring and the surface area of exposed active substance increases on moving away from the centre. Such a construction is however complex and difficult to manufacture using conventional techniques. Equally, U.S. Pat. No. 3851648 discloses a coated controlled release device whereby the exposed surface area of active substance increases with time in an attempt to counteract the increasing diffusion path between the aperture and the dissolving surface of the active substance. This document mentions a cylindrical device in which an aperture runs along the length of the cylinder, the aperture defining a cavity in which the surface area of active substance increases towards and beyond the central axis of the cylinder. Again, this is a complex configuration which is difficult to manufacture and, like the device described in EP-A-259219, such a system does not consistently provide a constant or predetermined controlled release of active substance.

EP-B-259113 describes a controlled-release device in which the active substance is present as a truncated cone surrounded by an impermeable coating, the smaller end of the cone being exposed to the dissolving fluid. Devices are described in GB-A-1022171 in which the central core of active substance is accessed, through a fluid-impermeable coating, by means of a small opening in the coating. Again, such complex configurations cannot be produced in a single step using conventional tablet-making techniques nor do they achieve a consistent level of the intended constant release.

EP-A-432607 discloses a controlled-release tablet having a core comprising active substance together with swelling and gelling agents, the core being surrounded by a slowly soluble polymeric coating having an aperture therein allowing exposure of a surface of the core. Hydration of the core and not the geometry of the cavity controls the release kinetics. FIG. 2 of this document reveals a "sandwich" tablet construction but the release kinetics are controlled by hydration of the core and not the geometry of the cavity.

U.S. Pat. No. 4792448 describes a coated right cylinder having an exposed circumferential strip, fluid dissolving its way through the active substance into the interior in an essentially unguided manner.

In general, however, none of these systems has a predetermined, controlled rate of release. Also, none of the above prior an systems combine effectiveness with simplicity of manufacture.

There is therefore a need to provide an improved constant-release device, in which the above-mentioned problems are largely obviated. The present invention addresses these problems.

Thus, according to a first aspect, the present invention provides a device for the release of at least one active substance into a fluid medium by dissolution of said active substance in said medium, said device comprising a covering, which is impermeable to said active substance and to said fluid or is swellable or slowly soluble in said fluid, having at least one aperture therein and defining a shaped cavity, said cavity being filled by a shaped core comprising uniformly disposed active substance, whereby on exposure of the device to said fluid medium a surface of said core is exposed to said fluid medium via said aperture and dissolution of said surface by said fluid medium causes a change in at least one dimension of the area of said surface whilst the surface area of said exposed surface remains substantially constant over at least 50% of the total dissolution time of said core.

Thus, the geometry of the device is such that, by maintaining a constant surface area of exposed active substance for a significant period, it achieves a constant release of active substance over that period—this control over the release rate is a significant improvement over the prior art devices. Furthermore because at least one dimension changes (in contrast to cylindrical cores exposed at one end, as shown in for example FIG. IX of GB-A-1022171, the shape is such that the active substance cannot "fall out" of the covering, and so there is no "dose dumping". Moreover, substantially all of the active substance is released.

The operation of the "dissolution device" according to the invention is believed to be based largely on the following theoretical considerations:

For a core with a uniformly disposed active substance and with a uniform rate of mass erosion, the rate of release of active substance, dim, dt from a compressed soluble disc, when governed by dissolution, may be expressed as $$\frac{dm}{dt} = A \cdot \frac{dx}{dt} \cdot C$$

[wherein dx is the mass erosion rate; and dt
A is the surface area, and C is the concentration of active substance].

Thus, there will be a constant rate of dissolution provided the surface area is kept constant, active substance is uniformly distributed within the compact and erosion is uniform. Whilst the rate of dissolution is in reality a complex function of the changing size and shape of the compact of active substance and the fluid dynamics of the adjacent dissolution medium layer, it has now been found that, as a practical matter, the surface area will be the rate-determining factor, in respect of dissolution of active substance, provided the geometry of the system is designed so as to create the appropriate conditions. The device of the present invention substantially eliminates the problem of irregular erosion caused by changing hydrodynamic conditions of the dissolving medium for example in turbulent conditions in the alimentary system, thus producing consistent zero order release of active substance, and thus providing a device wherein release of active substance is amenable to greater control than in those of the prior art.

The surface area of the exposed active substance remains substantially constant over at least 50% of the total dissolution time of the core, preferably at least 60%, more preferably at least 70%, even more preferably at least 90% of the total dissolution time of the core. Indeed, it is possible to achieve a constant surface area over 95% to substantially 100% of the total dissolution time of the core of active substance.

The geometrical profile of the cavity and active substance core may be such that "pulses" of active substance are released at predetermined points in the total dissolution time. Thus, the profile of the cavity "walls" may be varied to provide pre-determined changes in the surface area so as to provide pulses of activity, for example an initial dose of active substance. In a modification of the device, the core may comprise layers of two or more different substances, each layer containing the active substance uniformly disposed therein. Furthermore, the whole device may be provided with an outer soluble coating which provides an initial delay before release of active substance begins, or alternatively provides an immediate dose of active substance.

It is generally preferred that the aperture(s) be large enough so that the length of the diffusion pathway from the dissolving core to the aperture is not the rate-determining factor for the release of active substance. Equally, it is preferred that the aperture be large enough to not significantly restrict the egress of dissolved active substance or ingress of dissolving fluid.

In order to maximise the constant release of the active substance, it is particularly preferred that the exposed surface of active substance be accessible to the dissolving fluid medium via the aperture(s) from two or more directions.

In a further or alternative aspect the present invention provides a device for the release of at least one active substance into a fluid medium by dissolution of said active substance in said medium, said device comprising a covering, which is impermeable to said active substance and to said fluid or is swellable or slowly soluble in said fluid, having at least one aperture therein and defining a shaped cavity, said cavity being filled by a shaped core comprising active substance disposed, preferably uniformly, in a matrix of an inert excipient insoluble in said fluid, said device being axially symmetrical, with said aperture being peripherally disposed so that the release surface of core which is exposed through said aperture is substantially cylindrical or part of a cylinder in shape, whereby to allow substantially constant release of said active substance over at least part of the dissolution time.

In such a "diffusion device" the shaped core thus comprises a soluble active substance disposed in an insoluble matrix. The matrix remains intact and retains its shape during the time during which all of the active substance dissolves into the surrounding medium. The "dissolution front" is the surface of active substance which is in contact with the surrounding medium. Initially, the diffusion front and the release surface (of the core) are the same. During diffusion of the active substance, the diffusion front moves away from the aperture towards the centre of the core, leaving the release surface at the aperture. Thus, the active substance goes into solution at the diffusion from and diffuses through the pores of the matrix to be leached out at the exposed surface (the release front).

The diffusion device according to the invention is particularly suitable for the delivery of highly potent active substances, where only small doses of active ingredient are required, or where the active substance is to be released over an extended time period, for example up to 12 hours.

The "diffusion device" of the present invention provides an effective controlled release of active substance, has a geometry such that, on passage of the device through the alimentary canal, the release surface remains accessible to the surrounding fluid thus maintaining a constant rate of release, and is of a geometry such that it can be easily manufactured on a conventional multi-layer tablet press.

Because of the geometry of the diffusion device, the rate of release will conveniently remain constant until about 75% of the active substance has been released. Beyond this, there will be a gradually decreasing rate of release in the central "columnar" portion of the core.

The operation of the diffusion device is believed to be based largely on the following theoretical considerations:

For a core with an active substance uniformly disposed in a matrix of insoluble substance, $$\frac{dq}{dt} = -D \cdot A \cdot \frac{dc}{dr}$$

[wherein q is the mass of active substance transferred;
t is the time;
c is the concentration of active substance;
r is the distance from the aperture and the release surface to the diffusion front;
A is the surface area of the diffusion front; and
D is the diffusion coefficient for the active substance].

Thus, generally, in a diffusion-controlled system the release rate will decrease as r increases. The release rate is maintained at a constant value, in the present invention, through increase in the surface area of the diffusion front which compensates for the increase in diffusion distance of the active substance being transported. This is achieved through the profile of the cavity walls of the device of the present invention. The profile of the cavity walls of the diffusion device according to the invention may be concave, convex or linear.

Preferably, the profile of the cavity walls is such that at least one of the core surfaces in contact with the covering is concave over at least 25 percent, preferably 50 to 75 percent, e.g. 75% of the distance from the aperture to the centre of the core.

The geometrical profile of the cavity and core of the diffusion device may be such that "pulses" of active substance are released at predetermined points in the total dissolution time. Thus, the profile of the cavity "walls" may be varied to provide pre-determined changes in the surface area so as to provide pulses of activity. In a modification of the device, the core may comprise layers of two or more different active substances, each layer containing the active substance uniformly disposed therein. Furthermore, the whole device may be provided with an outer soluble coating which provides an initial delay before release of active substance begins, or alternatively provides an immediate dose of active substance.

Preferably, the profile of the cavity walls adjoining the aperture will be concave.

It is generally preferred that the aperture(s) be small enough so that the length of the diffusion pathway from the diffusion from to the aperture and the release surface is the rate-determining factor for the release of active substance.

In order to maximise the constant release of the active substance, it is particularly preferred that the diffusion from be accessible to the dissolving fluid medium via the aperture(s) from two or more directions.

The covering of both the dissolution and diffusion devices of the invention may comprise any active substance impermeable material which is either impermeable to fluid or is swellable or slowly soluble in the fluid, which can be formed into a solid. By "slowly soluble" it is meant that the covering has a slower dissolution rate than that of the tablet core. By "impermeable" it is meant that the covering is impermeable to fluid for the dissolution life of the device. The material is preferably biodegradable so that it may degrade after substantially all the active substance has dissolved; thus for example, the material may be one or more biodegradable polymers such as polyglycolide, poly (L-lactide), poly (DL-lactide), caprolactone, polyanhydrides, poly (orthoesters) and poly (amino acids). Examples of other useful polymers which may not be biodegradable are ethyl cellulose, cellulose acetate phthalate, cellulose acetate, cellulose acetate butyrate, methacrylic acid copolymers, hydroxypropyl methylcellulose acetate phthalate, polyvinyl acetate phthalate, Eudragit RS, Eudragit RL, polypropylene or polyethylene. Combinations of two or more of such substances may be used.

Preferred covering materials include cellulose acetate, cellulose acetate butyrate and cellulose acetate phthalate and methacrylic acid copolymers, or mixtures thereof.

Fluid (e.g. water)-swellable coverings should generally be swellable in one direction such that the geometric configuration of the device is not altered and there is still adhesion between the covering and the tablet core. Such coverings have the advantage that they do not leave a residue once the active substance has been fully released. Furthermore such swellable polymers tend to adhere to the wall of the intestine preventing the device from passing through the g.i. tract. Absorption of substances such as ranitidine may thereby be enhanced.

The other substances that may be present in the covering with the above-mentioned substances will depend on the technique used to encase the core of active substance with the covering. The covering material may be blended with one or more excipients and then compressed onto a pre-shaped core of active substance. Compressions may be effected directly onto the core of active substance with a compression coating machine. The devices of the invention have the particular advantage that pharmaceutical devices which are tablet-sized may be easily manufactured using a conventional tabletting machine or a compression coating machine. Indeed, the manufacture of such devices is highly reproducible. Thus, it is possible to manufacture a plurality of such devices for the release of at least one active substance into a fluid medium by dissolution or diffusion wherein the maximum variation in performance of the tablets does not exceed 5 to 10%. "Plurality of devices" includes a production run of such devices, a course prescribed by a medical practitioner, or a bottle, container, packet or batch of such devices.

Three preferred coating techniques for compression onto a pre-formed core are as follows:
1. Blending an excipient with a binder and granulating the blend with a granulating solution in which the excipient may or may not be soluble; drying, sizing and lubricating the granulated material; and, with the aid of a compression coating machine, forming a casing having an appropriate aperture(s) around the pre-shaped core of active substance from the sized granules.
2. Mixing a blend of soluble or insoluble and soluble polymers with a plasticizer and allowing the blend to stand for at least 24 hours; with the aid of a compression coating machine, forming a casing having an appropriate aperture(s) around the pre-shaped core; heating the coated tablets to a temperature at which the polymer forms a continuous film (e.g. 50°–140° C. for 1 to 30 min).

3. Mixing a blend of soluble or insoluble and soluble polymers with a lubricant and, with the aid of a compression coating machine, forming a casing having an appropriate aperture(s) around the pre-shaped core.

Suitable binders for the covering include, for example, methylcellulose, hydroxypropyl cellulose, hydroxypropyl methylcellulose, acacia, gelatin, tragacanth, polyvinyl alcohol, glucose, sucrose, dextran and polyvinyl pyrrolidone.

Suitable lubricants for the covering are, for example, sodium stearate, sodium stearyl fumarate, Carbowax 4000, Carbowax 6000, sodium lauryl sulfate, magnesium lauryl sulfate and sodium oleate.

Colours and flavourings may be present in the covering.

When required, suitable plasticizers that may be used include diacetin (glyceryl diacetate), triacetin (glyceryl triacetate), diethyl phthalate, dibutyl phthalate, glycerol tributyrate, triethyl titrate, ethyl lactate, polyethylene glycol 600, propylene glycol, diethyl tartrate, ethylene glycol monoacetate and dibutyl sebacate.

Dissolution cores may comprise solely active substance or the active substance may be present with binders and/or inert soluble excipients.

In the devices of the invention, the core of active substance or the polymer matrix in which the active substance is dispersed may imbibe fluid to a small extent, but the configuration of the system should remain intact and dissolution of the active substance should occur only at the exposed surface or diffusion front as appropriate. The active substance of the core should be uniformly dispersed. This will generally mean that the core has been uniformly compacted, with no changes in compaction that would lead to irregularities in the rate of dissolution or diffusion.

In order to prepare cores for the dissolution device according to the invention the active substance may be blended with one or more excipients and then compressed into the desired shape, for example easily by means of a conventional tabletting machine/press.

A preferred technique for producing cores of active substance for dissolution devices is the following:
1. A water soluble binder and a water soluble diluent and optionally the active substance are mixed in a suitable blender and the mixture is sized through a screen.
2. The drug, if not included with the binder and the diluent in 1, is dissolved in an appropriate amount of pharmaceutically acceptable solvent and the solution is used to granulate the blend prepared as described in 1.
3. The granulate is dried and sized and optionally regranulated.
4. The sized granulation is mixed with a soluble lubricant and the lubricated mixture is compressed into a tablet core of the appropriate shape.

Soluble diluents that may be used in the dissolution core include lactose, fructose, mannitol, sorbitol, calcium sulfate and magnesium sulfate.

Binders that may be used in the dissolution core include methylcellulose, hydroxypropyl cellulose, hydroxypropyl methylcellulse, acacia, gelatin tragacanth, polyvinyl alcohol, glucose and sucrose.

Solvents that may be used in the dissolution core include water, methanol, ethanol and isopropyl alcohol.

Lubricants that may be used in the dissolution core are sodium stearate, carbowax 4000, Carbowax 6000, sodium lauryl sulfate, magnesium lauryl sulfate and sodium oleate.

The diffusion device according to the invention may be manufactured either by compressing the covering onto a pre-pressed core, or by compressing layers of granulated covering and core on a multi-layer tablet press into the desired shape.

A preferred procedure for preparing a pre-formed core is as follows:
1. Blending soluble active substance and an insoluble matrix material, e.g. a polymer, and then sizing the mixture through an appropriate size screen. The blend may be wetted with water or granulated with a water insoluble polymer dissolved in an appropriate solvent, or with an otherwise suitably prepared polymer dispersion.

Alternatively, the drug may be dissolved in an appropriate amount of pharmaceutically acceptable solvent, conveniently water, and the solution spread uniformly on the insoluble polymer.

2. Drying the granulate, as required, at a suitable temperature and sizing through a suitable size screen.
3. The sized granulate in step 2 may be rewetted and step 2 repeated.
4. Mixing the sized granulate with a lubricant and compressing the lubricated mixture into a tablet core of the desired shape.
5. Compression coating the core thus formed using a compression coating machine as described hereinbefore.

For compression of a granulated core material with a granulated covering material on a multi-layer press, a preferred procedure is as follows:
(a) Steps 1, 2 and 3 are the same as described above.
(b) The sized granulate is mixed with a lubricant and the lubricated mixture is reserved for use in Step (d).
(c) The covering material is prepared as described hereinbefore.
(d) An appropriate amount of the covering material is loaded in the die of a triple layer machine. This is followed by the required amount of the active substance mixture from step (b) and then again the covering material in an amount equal to the first layer.
(e) The punches are brought together to compress the tablet.

The diffusion core may comprise ethyl cellulose, cellulose acetate butyrate, methacrylic acid copolymers, polypropylene or polyethylene. Biodegradable polymers which may also be used include polyglycolide, poly (L-lactide), poly (DL-lactide), caprolactone, polyanhydrides, poly (orthoesters) and poly (amino acids). Combinations of two or more of such substances may be used.

Lubricants that may be used in the diffusion core are sodium stearate, Carbowax 4000, Carbowax 6000, sodium lauryl sulfate, magnesium lauryl sulfate, sodium oleate, magnesium stearate, calcium stearate, zinc stearate, stearic acid, hydrogenated vegetable oils, mineral oil, glyceryl palmitostearate and glyceryl behenate.

When required, suitable plasticizers that may be used for the diffusion core are as described hereinbefore for the covering.

Binders that may be used for the diffusion core include ethylcellulose, cellulose acetate, cellulose triacetate, cellulose acetate butyrate and methacrylic acid copolymers.

Solvents that may be used for the diffusion core include water, methanol, ethanol, isopropyl alcohol, acetone, ethyl lactate and methylene chloride.

The active substance may be any appropriate fluid-soluble active substance. Thus, the active substance may be a pharmaceutically active substance. Alternatively, the device may be used, with the appropriate active substance, in the dispensing of insecticides, pesticides, perfumes, and water treatments with germicides in swimming pools, toilets etc.

Pharmaceutically active substances which may be employed in the tablet cores include a wide range of inorganic and organic pharmaceutical agents such as muscle-relaxants, anti-Parkinson agents, analgesics, anti-inflammatory agents, muscle contractants, hormonal agents, contraceptives, diuretics, electrolytes, bronchodilators, antihypertensives, hypnotics, steroids, serotonin agonists or antagonists and $H_2$-antagonists.

Preferred active ingredients include bronchodilators such as salbutamol, antihypertensives such as labetalol, anti-migraine compounds such as serotonin agonists, e.g. sumatriptan and pharmaceutically acceptable salts and solvates thereof, e.g. the succinate, $5HT_3$ serotonin antagonists such as ondansetron and pharmaceutically acceptable salts and solvates thereof, e.g. the hydrochloride dihydrate, 2,3,4,5-tetrahydro-5-methyl-2-[(5-methyl-1H-imidazol-4-yl)methyl]-1H-pyrido[4,3b]indol-1-one and pharmaceutically acceptable salts and solvates thereof, e.g. the hydrochloride salt, (+)-1,2,3,9-tetrahydro-9-methyl-3-[(5-methyl-1H-imidazol-4-yl)methyl]-4H-carbazol-4-one and pharmaceutically acceptable salts and solvates thereof, e.g. the hydrochloride salt, 6-fluoro 2,3,4,5-tetrahydro-5-methyl-2-[(5-methyl-1H-imidazol-4-yl)methyl]-1H-pyrido[4,3-b]indol-1-one, and pharmaceutically acceptable salts and solvates thereof, $H_2$-antagonists such as ranitidine, cimetidine, sufotidine, famotidine, roxatidine or nizatidine.

Further preferred active ingredients include salbutamol, labetalol and, more particularly, ranitidine.

As mentioned above, the term 'ranitidine' encompasses pharmaceutically acceptable salts thereof. Such salts include salts with inorganic acids, such as hydrochlorides, hydrobromides and sulphates, and organic acids, such as acetates, maleates, succinates, fumarates and ascorbates. A particularly preferred salt is the hydrochloride.

The devices according to the invention may be adapted to provide a variety of unit doses depending on the active ingredient and the age and condition of the patient. Suitable doses will be readily appreciated by those skilled in the art.

When the devices according to the invention contain ranitidine, a convenient unit dose of ranitidine is 50–800 mg, preferably 75–600 mg, e.g. 150 mg, 300 mg or 600 mg, expressed as the weight of the free base. Such unit doses may be administered one to four times a day, preferably once or twice a day.

BRIEF DESCRIPTION OF THE DRAWINGS

The invention will now be illustrated with reference to the accompanying drawings, in which:

FIG. 1b is a schematic vertical cross-section through a tablet comprising the core of FIG. 1a.

FIG. 2b is a schematic cross-section through a tablet comprising the core of FIG. 2a.

FIG. 4a–c is a schematic representation illustrating the operation of a diffusion tablet according to a second embodiment of the invention, i.e. the device of FIG. 1d.

FIG. 9 shows a graph of % ranitidine hydrochloride released vs. dissolution time (minutes) for Example 5.

FIG. 10 shows a graph of % ranitidine hydrochloride released vs. dissolution time (minutes) for Example 6.

FIG. 11 shows a graph of % salbutamol sulphate released vs. dissolution time (minutes) for Example 7.

FIG. 12 shows a graph of % salbutamol sulphate released vs. dissolution time (minutes) for Example 8.

Referring to FIG. 1a, there is provided, according to a preferred embodiment, a core of uniformly disposed active substance 1 comprising a body of active material, optionally disposed in a fluid insoluble matrix, 2 having a central cylindrical bore 3. The body of material 2 has a cylindrical face 4 and concave surfaces 5,6. When coated, the cylindrical surface 4 is the only exposed surface.

Referring to FIG. 1b, the body of active material 2 is surrounded by an active substance fluid-impermeable, water-swellable or very slowly soluble (slower dissolution rate than that of the tablet core) covering 7, except for the exposed cylindrical face 4. The covering 7 fills the cylindrical bore 3 and therefore acts as a central pillar holding the disc of active substance.

In this embodiment, the diameter, DC, of the bore 3 is equal to the thickness, Hp, of cylindrical face 4, and the height, Ht, of the bore 3 is equal to the diameter, Dt, of the body of active material 2. These dimensions are preferred. Devices having the core shape of this embodiment are particularly suited to dissolution cores.

When exposed to the dissolving fluid, the cylindrical face 4 of active substance dissolves and Dt decreases whilst Hp increases, i.e. the diameter of the body of active substance decreases and the peripheral edge with increasing height is continuously exposed.

Figure 1A:
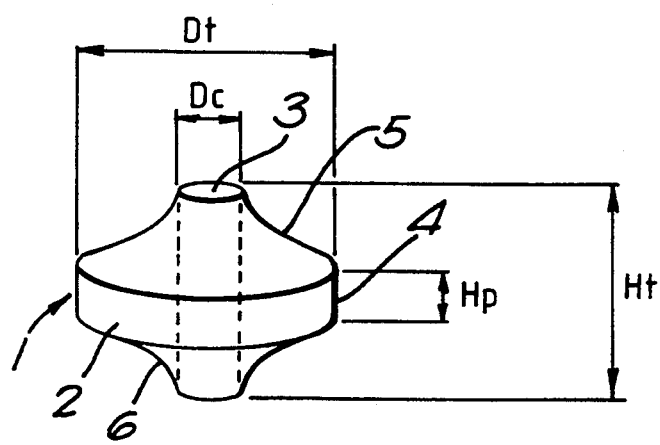
FIG. 1a is a schematic representation of an active substance dissolution or diffusion core according to one embodiment of the invention (first embodiment).
Figure 1B:
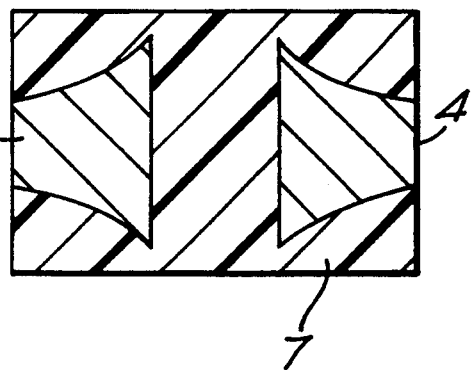
Figure 1C:
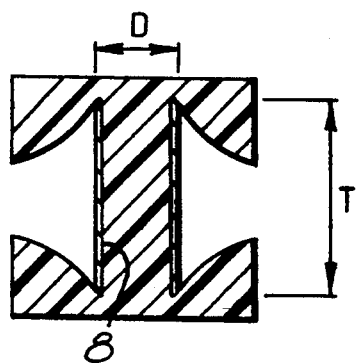
FIG. 1c is a schematic cross-section through the tablet of FIG. 1b when filled with a dissolution core after dissolution of a portion of the active substance.

Referring to FIG. 1c, immediately prior to the end of the dissolution process, the diameter D of the body of active substance 8 is nearly equal to the initial peripheral thickness Hp of the active portion, and the thickness T is nearly equal to the height, Ht, of the cylindrical bore.

Throughout the dissolution process the product of height and diameter (which, when multiplied by pi is equal to the surface area) remains constant and the rate of release of drug remains constant until substantially all of the drug has been dissolved.

Figure 1D:
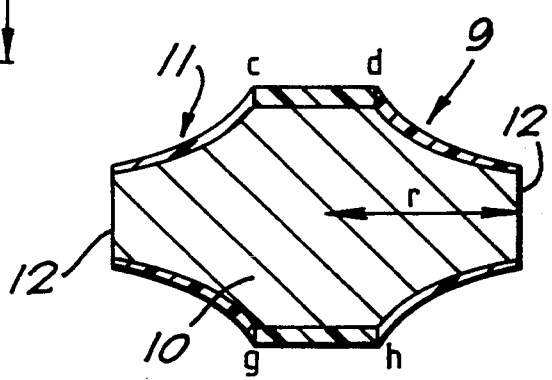
FIG. 1d is a schematic vertical cross-section through a diffusion tablet according to a further embodiment of the invention (second embodiment) manufactured by compressing powders on a multilayer press.

FIG. 1d shows a second preferred embodiment (second embodiment) of the present invention. There is provided a tablet 9 comprising a body 10 of active material, disposed in a fluid-insoluble matrix, surrounded by an active substance fluid-impermeable, water-swellable or very slowly soluble (slower dissolution rate than that of the tablet core) covering 11, except for the exposed cylindrical face 12. Such a configuration has the advantage that it can be conveniently prepared on a multi-layer press.

FIG. 2 (a-c) shows a third preferred embodiment (third embodiment) of the present invention.

Figure 2A:
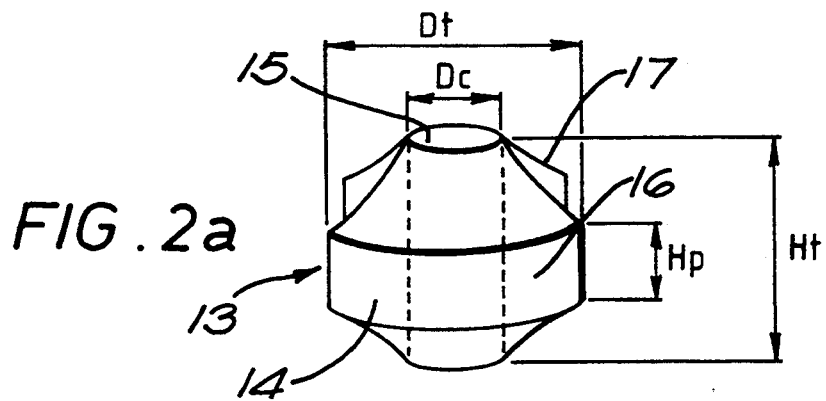
FIG. 2a is a schematic representation of an active substance dissolution or diffusion core according to a third embodiment of the invention (third embodiment).

Referring to FIG. 2a, the body of uniformly disposed active material 13 comprises a body of active material, optionally disposed in a fluid-insoluble matrix, 14 formed of two segments 16, 17 of the core shown in FIG. 1a, with a cylindrical bore 15. Such a configuration has the advantage that the strength and integrity of the covering is greatly increased.

Figure 2B:
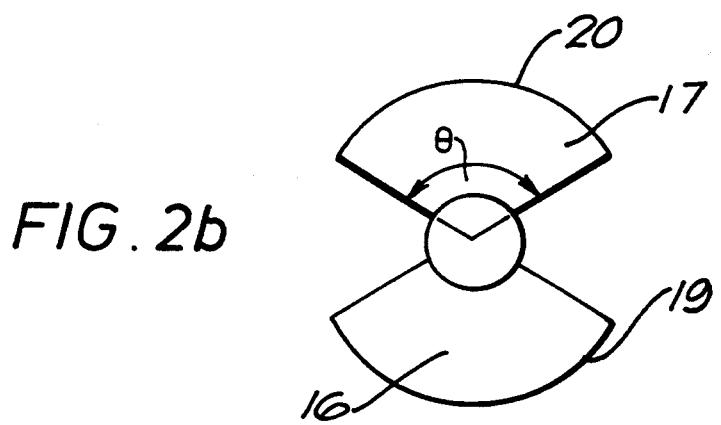
Figure 2C:
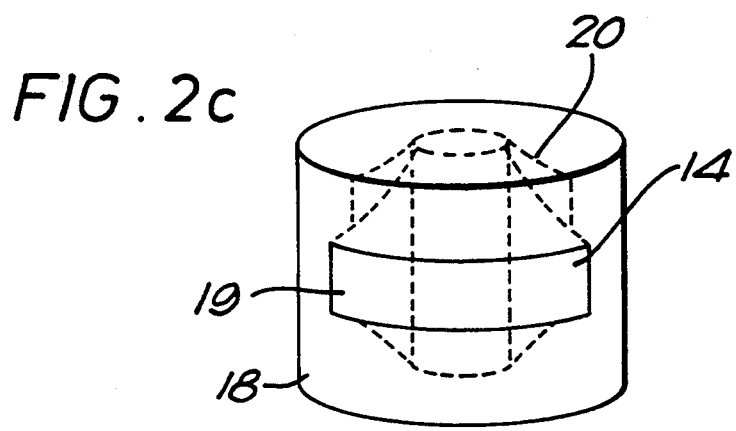
FIG. 2c is a schematic representation of the tablet of FIG. 2b.

FIG. 2c shows a corresponding tablet configuration for the third embodiment. The body of active material 14 is surrounded by a fluid-impermeable, water-swellable or very slowly soluble (slower dissolution rate than that of the tablet core) coating 18, which also fills the cylindrical bore 15. This leaves two exposed curved faces of active substance 19, 20.

Referring to FIGS. 2b (and 2a), and for a dissolution core device, dissolution of the surfaces 19, 20 of the core segments 16, 17, proceeds inwards. Since the sector angle is constant, the surface area is $D t \times H p \times \theta$ (where $\theta$ is the sector angle in radians).

In order to maintain a constant surface area of exposed active substance, there is an inverse relationship between the height and the radius. As dissolution proceeds, the radius decreases and the height of the surface of exposed active substance increases, leading to constant surface area.

The above embodiments display a constant release over the whole of the dissolution time. However, particularly in the case of a dissolution device, beyond 50% of the dissolution time different release profiles may be incorporated in the device by varying the surface configuration of the cavity and therefore of the active substance core, i.e. by varying the change of height Hp with distance from the periphery. This can be used, for example, to incorporate "bursts" of release of active substance on a background of otherwise constant release. The surface area of active substance should, however, be constant for at least 50% of the total dissolution time of the core of active substance.

Figure 3:
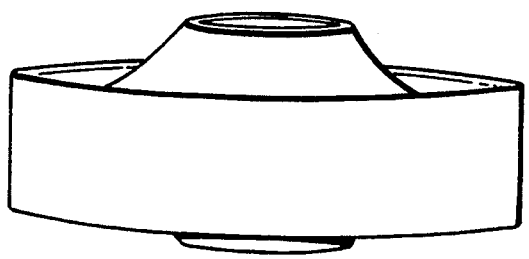
FIG. 3 is a side view of an active substance dissolution core according to a fourth embodiment of the invention (fourth embodiment).

Referring to FIG. 3, there is provided according to a fourth preferred embodiment (fourth embodiment) of the invention, the core of a dissolution device which has been modified to provide an initial "burst" or "pulse" of active ingredient by increasing the height Hp at the periphery.

Thus such a device can be designed to release 20–50% (e.g. 30–50%) of the total active ingredient (e.g. ranitidine) in the first hour (e.g. in the first 30 minutes) followed by constant release of the remaining 50–80% (e.g. 50–70%) active material over the next 1–5, e.g. 3–5 such as 4–5, hours.

Figure 3A:
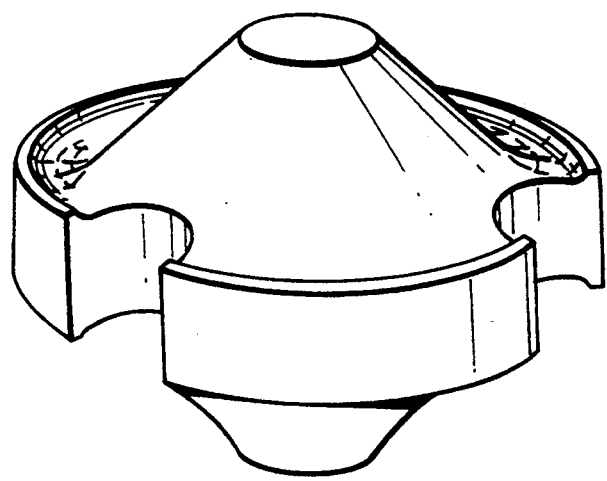
FIG. 3a is an oblique view of an active substance dissolution core according to a fifth embodiment of the invention (fifth embodiment).

With reference to FIG. 3a, there is provided according to a fifth preferred embodiment (filth embodiment) of the invention, a further dissolution device core modified to provide an initial burst of active ingredient, and having three hemispherical grooves in the periphery at 120° to each other, which serves to improve the integrity of the covering when applied to the core.

With reference to FIG. 4 a-c, when exposed to the surrounding medium the active substance leaches out from the cylindrical face 12. The diffusion front begins to recede and move inwards, i.e. the distance (r) from the diffusion front to the release surface (ab) increases but, the diffusion front with increasing surface area is continuously exposed to the medium. The increase in surface area of the diffusion front compensates for the increase in (r) and maintains a constant release rate until the dissolving medium reaches the area under cdgh. At this point the surface area to the diffusion front begins to decrease, producing a decrease in release rate, until all of the drug is exhausted.

Referring back to FIG. 1d, the components of the covering 11 in powder form are loaded in the die of a triple layer tabletting press. The mixture of core 10 compounds in powder form is then introduced as a middle layer and finally another layer of covering 11 in powder form is introduced. The tooling of the tabletting press is such that the core layer is held in the desired geometric configuration. The punches are then brought together to compress the layers into a tablet.

In the above-mentioned embodiments, the dissolving surface or diffusion front of active substance is protected from at least two directions by the covering. This helps in minimizing the effect of variation in hydrodynamic conditions of the adjacent fluid on the dissolving surface or diffusion front and therefore favours a more uniform rate of dissolution of the active substance.

It is particularly preferred that the device as used for pharmaceuticals and, indeed for other uses, is axially symmetrical, i.e. approximately cylindrical, although sectors of the cylinder may be omitted in some embodiments. The aperture in such devices is then preferably peripheral, that is a strip of the impermeable coating around the curved surface of the cylinder is omitted to expose an edge of the core of active substance. In a cylindrical device of this type, the impermeable covering coating the 'ends' of the cylinder are preferably joined or supported by a central column so that the core itself is a ring or toroid; this preserves the integrity of the covering in the latter stages of dissolution of the core. However, such a central column does not have to be present, so that the core may be whole—the advantage of such a configuration is that tablets may be produced in a single operation in a conventional multilayer press. Thus, for example, in FIG. 1a, the whole of the core 1 (including the central bore 3) may be an active substance-containing solid or fluid insoluble matrix.

In a toroidal dissolution device, the profile of the diametric cross-section of the core should be such that the height increases with distance from the aperture to compensate for the diminution of the circumference of the core as its exposed surface dissolves. For constant rate of release in such an axially symmetrical device, the height of the core at any radial distance from the centre should be proportional to the inverse of that radial distance, in order to maintain a constant exposed area of core as it dissolves. It is possible, however, to build into the profile of the core axially symmetrical irregularities which will give bursts or pulses in release of active material.

It is particularly preferred that the ratio of the diameter of the central column to the height of the aperture, and the height of the column to the diameter of the core of active material both be in the range 3:2 to 2:3, e.g. 1:1.

In general, the profile of the core and the width of the aperture will be such that the exposed surface of the core as it dissolves remains approximately cylindrical (or part of a cylindrical surface) as compared with the radially curved surface formed when a coated right cylinder has an exposed circumferential strip (as in U.S. Pat. No. 4,792,448) and the fluid dissolves its way into the interior in an essentially unguided manner. In the 'cylindrical' devices of the invention the impermeable coating provides a constraint upon the extent of dissolution in the axial direction which maintains an essentially cylindrical dissolving surface.

Where sectors are absent from an otherwise axially symmetrical core, the impermeable coveting will cover the radially directed sides of the sectorial spaces to define sections of core (which are, themselves sectors) so that the disclosing surface of the core is constrained circumferentially and maintains a controlled surface area.

For medicinal or veterinary use, such devices are particularly suitable as orally administrable dosage units, which may release their contents at various locations throughout the alimentary canal.

The foregoing description has been largely directed to the use of the device in respect of pharmaceutical and veterinary applications. However, there is a wide range of uses of such devices outside of these areas as noted earlier.

The following non-limiting Examples illustrate the invention:

EXAMPLE 1

Dissolution Core Containing Salbutamol Sulphate

Lactose 180 g, hydroxypropyl cellulose 60 g and salbutamol sulphate 13.15 g were wet granulated with water. The granules were sized through a 40 mesh (425 $\mu$) screen and lubricated with 1% (w/w) of sodium stearate. The lubricated granules were compressed into tablet cores of the shape shown in FIG. 1a.

The core weight was 155 mg and the diameter 8 mm.

Coating 70g of cellulose acetate CA398-10 and 30 g of cellulose acetate phthalate, both sized through 200 mesh, were thoroughly blended. The blend was granulated with 43 g of glyceryl triacetate and sized through a 20 mesh (850 $\mu$) screen. The sized granules were allowed to stand at room temperature for 24 hours. The granules were then used to encase the cores using an 8.1 mm standard concave punch. The coated cores were heated at 100° C. for 10 minutes to allow the polymer particles to fuse with each other and form a continuous layer. The coated tablet weight was 325 mg.

Dissolution

Figure 5:
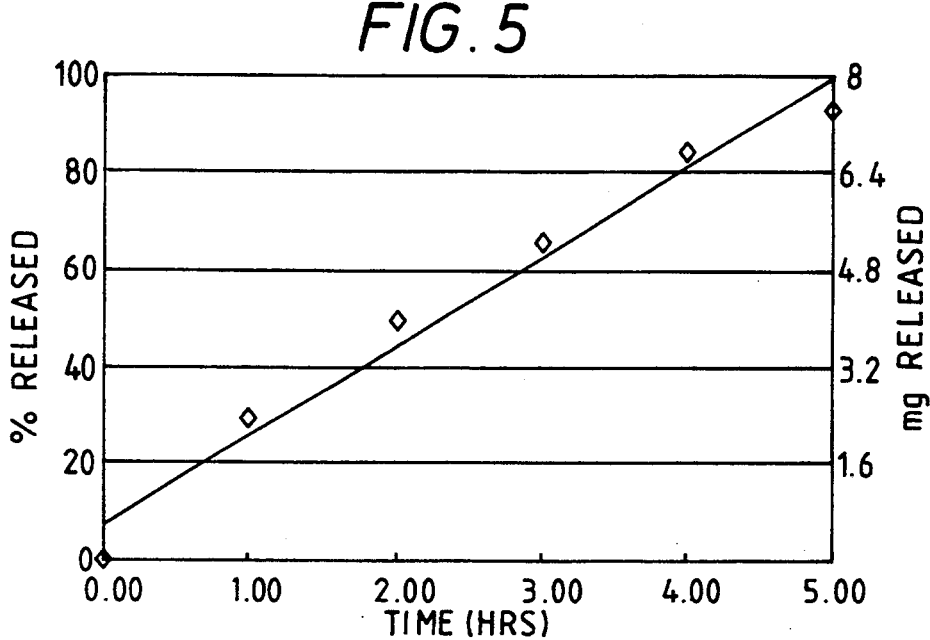
FIG. 5 shows a graph of % salbutamol sulfate released vs. dissolution time (hours) for Example 1.

The dissolution profile of the coated tablets was obtained in water using the USP apparatus 2. The graph shown in FIG. 5 shows a constant release profile (zero-order release kinetics) of the drug over a 5 hour period. All of the drug is released in that time at a rate of 1.491 mg/hr. The correlation coefficient of the straight line relationship is 0.9937.

EXAMPLE 2

Dissolution Core Containing Salbutamol Sulphate

Lactose 150 g, hydroxypropyl cellulose 50 g and salbutamol sulphate 10.5 g were wet granulated with water. The granules were sized through a 40 mesh (425 $\mu$) screen and lubricated with 1% (w/w) sodium stearate. The lubricated granules were compressed into tablets of the shape shown in FIG. 2a.

The core weight was 115 mg and the diameter 8 mm.

Coating

The coating formulation described in Example 1 was used to encase the cores using an 8.1 mm standard concave punch. The coated tablet weighed 275 mg.

Dissolution

Figure 6:
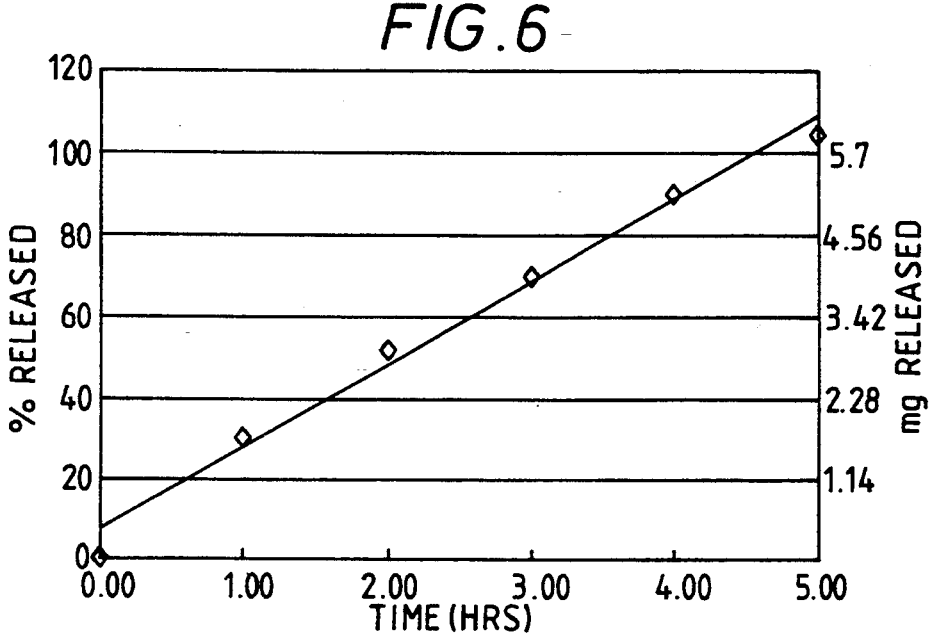
FIG. 6 shows a graph of % salbutamol sulfate released vs. dissolution time (hours) for Example 2.

The dissolution release profile of these tablets was obtained in water using the USP apparatus 2. The graph shown in FIG. 6 depicts a constant release profile of the drug over a 5 hour period. All of the drug is released in that time at a rate of 1.178 mg/hr. The correlation coefficient of the straight line relationship is 0.9875.

EXAMPLE 3

Dissolution Core Containing Labetalol Hydrochloride

Lactose 66.8 g, hydroxypropyl cellulose 46 g, polyvinyl alcohol 3 g and labetalol hydrochloride 83.2 g were granulated with water. The granules were screened through a 40 mesh (425 $\mu$) screen and lubricated with 1% (w/w) of sodium stearate. The lubricated granules were compressed into tablet cores of the shape shown in FIG. 1a.

The core weight was 100 m and the diameter 6.8 mm.

Coating

The coating formulation described in Example 1 was used to encase cores using a 6.9 mm deep concave punch. The coated tablets weighed 220 mg.

Dissolution

Figure 7:
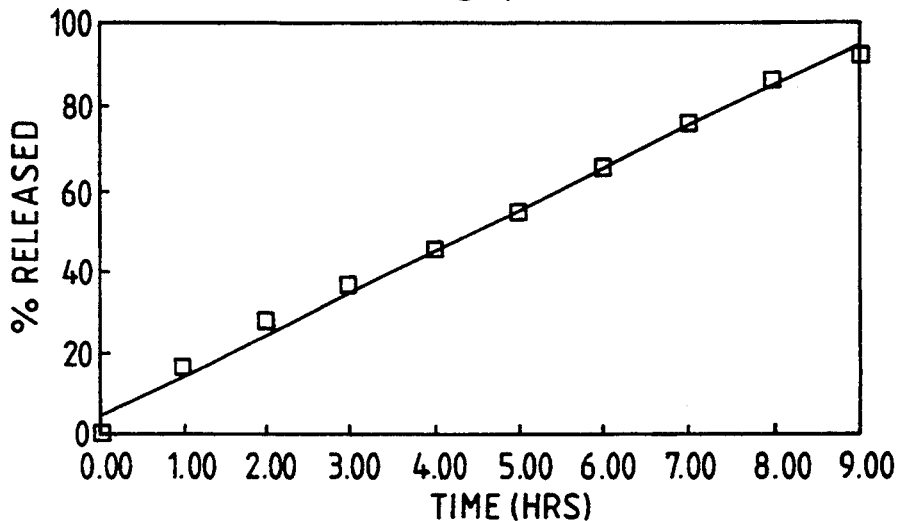
FIG. 7 shows a graph of % labetalol hydrochloride released vs. dissolution time (hours) for Example 3.

The dissolution profile of the coated tablets was obtained in water using the USP apparatus 2. The graph shown in FIG. 7 shows a constant release profile (zero-order release kinetics) of the drug over a 9 hour period. Nearly all of the drug is released in that time at a rate of 9.59%/hr. The correlation coefficient of the straight line relationship is 0.9952.

EXAMPLE 4

Dissolution Core Containing Ranitidine Hydrochloride

Lactose 30 g and hydroxypropyl cellulose 30 g were dry blended and wet granulated with water. The granules were dried and sized through a 40 mesh (425 $\mu$) screen. The sized granules were blended with ranitidine hydrochloride 140 g and the blend was granulated with methanol as the granulating agent. The granules were dried, sized and lubricated with 1.0 g of sodium stearate. The lubricated granules were compressed into tablet cores of the shape shown in FIG. 1a. The core containing 70 mg of ranitidine hydrochloride weighed 100 mg and the diameter was 6.8 mm.

Coating 70 g of cellulose acetate CA 398-10, after sizing through 200 mesh, was granulated with 30 g of glyceryl triacetate and passed through a 20 mesh (850 μ) screen. The sized granules were allowed to stand at an ambient temperature for 24 hours. The granules were then used to encase the cores using a 6.9 mm standard concave punch. The coated cores were heated at 100° C. for 10 minutes. The coated tablets weighed 240 mg.

Dissolution

Figure 8:
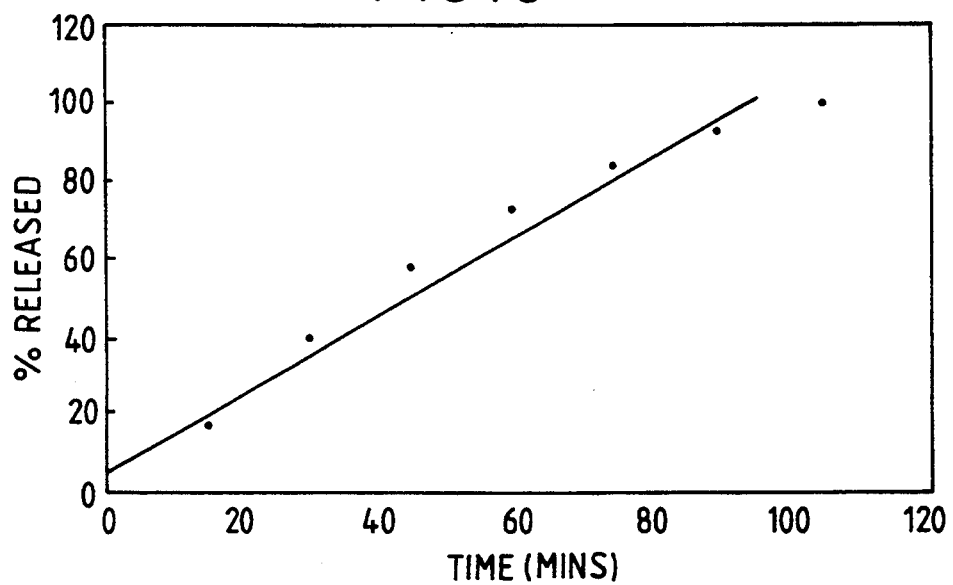
FIG. 8 shows a graph of % ranitidine hydrochloride released vs. dissolution time (minutes) for Example 4.

The dissolution profile of the coated tablets was obtained in gastric medium, pH 1.2, using USP apparatus 2. The graph in FIG. 8 shows a constant release profile (zero-order release kinetics) of the drug over a 105 minute duration. All the drug is released in that period at a rate of 0.678 mg/minute. The linear correlation coefficient of the straight line relationship is 0.9838.

EXAMPLE 5

Dissolution Core Containing Ranitidine Hydrochloride

Lactose monohydrate 84.76 g and hydroxypropyl cellulose 75.74 g were dry blended and the blend passed through a mill with a 0.75 mm screen. The sized blend was then mixed with 672.0 g of ranitidine hydrochloride and granulated with 180 g solution (5% w/w) of hydroxypropyl cellulose in isopropyl alcohol. The granules were dried and sized through a 20 mesh (850 μg) screen and lubricated with 8.5 g of sodium stearate. The lubricated granules were compressed, using core-rod punches, into 12.0 mm tablet cores of the shape shown in FIG. 3. The cores containing 336 mg of ranitidine hydrochloride (equivalent to 300 mg ranitidine free base) weighed 425 mg.

Coating 57.0 g of cellulose acetate butyrate and 3.0 g of sodium stearate were dry blended and the mixture passed through a 30 mesh screen. The upper and lower face of the core were encased with 150 mg of the coating material on each side using 12.15 mm standard concave punches. The compression coated tablet weighed 725 mg.

Dissolution

The dissolution profile of the coated tablets was obtained in gastric medium, pH 1.2, using the USP apparatus 2. The graph shown in FIG. 9 shows an initial rapid drug release, (30%) in the first 0.5 hr, followed by a constant release over the next 3 hours. The release rate of rantidine hydrochloride for the constant release portion is 75 mg/hr. The correlation coefficient of the straight line relationship for the constant release portion is 0.9827.

EXAMPLE 6

Dissolution Core Containing Ranitidine Hydrochloride

The core material was prepared as described in Example 5 and compressed using an adapted tooling to give a tablet core having a shape as shown in FIG. 3a. The core diameter was 12 mm.

Coating

The upper and lower face of the core, together with the hemispherical grooves, were encased with the coating material described in Example 5 using standard concave punches, as described in Example 5. The coated tablet weighed 725 mg and had a diameter of 12.15 mm.

Dissolution

The dissolution profile of the coated tablets was obtained in gastric medium, pH 1.2 using the USP apparatus 2. The graph in FIG. 10 shows an initial rapid release for 0.5 hr (26%), followed by a constant release over the next 3 hours. The release rate for the constant release portion is 70.4 mg/hr. The correlation coefficient of the straight line relationship for the constant release portion is 0.9971.

EXAMPLE 7

Diffusion Core Containing Salbutamol Sulphate

Cellulose acetate butyrate granules (184 g), were thoroughly wetted with a solution of salbutamol sulphate (16 g) in water containing 1% Spart 80 (Spart 80 is a brand of sorbitan mono oleate (suffactant) Supplier: ICI Speciality Chemicals, Atkemix Inc., Brantford, Ontario, Canada). The granules (A) were air dried overnight, sized through a 40 mesh (425 μm) screen and lubricated with 0.5% magnesium stearate. The lubricated granules were compressed into tablet cores of the shape shown in FIG. 1d. The core weight was 75 mg and the diameter was 6.8 mm.

Coating 70 g of cellulose acetate CA 398-10 was granulated with 30 g of glyceryl triacetate. The granules were sized through a 16 mesh (1180 μm) screen and allowed to stand at room temperature for 24 hours. The granules were screened again through a 40 mesh (425 μm) screen before being used to encase the cores. The cores were compression coated using a 6.9 mm standard concave punch. The coated tablets were heated to 100° C. for 10 minutes to allow the polymer particles to fuse together and form a continuous layer. The coated tablets weighed 144 mg.

Dissolution

The dissolution profile of the coated tablets was obtained in water using the USP apparatus 2. The graph in FIG. 11 shows an initial rapid release for 1½ hours followed by a constant release over the next 4½ hours. The correlation coefficient of the straight line relationship for the constant release portion is 0.9859. More than 90% of the drug is released within 6 hours. The release rate for the constant release portion is 0.6087 mg/hr.

EXAMPLE 8

Diffusion Core Granules (A) Containing Salbutamol Sulphate

Cellulose acetate butyrate granules (184 g), were thoroughly wetted with a solution of salbutamol sulphate (16 g) in water containing 1% Spart 80. The granules (A) were air dried overnight, sized through a 40 mesh (425 μm) screen and lubricated with 0.5% magnesium stearate.

Coating Granules (B)

Cellulose acetate CA 398-10 (70 g) was granulated with glyceryl triacetate (30 g) and sized through a 16 mesh (1180 μm) screen. The granules (B) were allowed to stand at room temperature for 24 hours and screened again using a 40 mesh (425 μm) screen.

Diffusion Device Formation

The tablets were compressed using triple layer compression techniques with each coating layer granules (B), upper and lower, weighing 25 mg and the active substance containing layer granules (A) weighing 62 mg. The one-step compressed core weighed 110 mg and the diameter was 6.8 mm. The shape is shown in FIG. 1d.

Dissolution

The dissolution profile of the triple layer compressed tablet was obtained in water using the USP apparatus 2. The graph in FIG. 12 shows an initial rapid release for 1½ hours followed by a constant release over the next 6 hours. The correlation coefficient of the straight line relationship of the constant release portion is 0.9893. More than 80% of the drug was released within 8 hours. The remainder of the drug was released at a decreasing rate over the next 4 hours. Thus 95% of the drug was released in 12 hours. The release rate for the constant release portion is 0.4637 mg/hr.

We claim:

1. A device for the release of at least one active substance into a fluid medium by dissolution of said active substance in said medium, said device comprising a covering, which is impermeable to said active substance and to said fluid or is swellable or slowly soluble in said fluid, having at least one aperture therein and defining a shaped cavity, said cavity being filled by a shaped core comprising said active substance, and wherein:
   a) said active substance is uniformly disposed in said core and whereby on exposure of the device to said fluid medium a surface of said core is exposed to said fluid medium via said aperture and dissolution of said surface by said fluid medium causes a change in at least one dimension of the area of said surface whilst the surface area of said exposed surface remains substantially constant over at least 50% of the total dissolution time of said core, said device being axially symmetrical, with said aperture being peripherally disposed so that the exposed surface of active substance core is cylindrical or part of a cylinder in shade; or
   b) said active substance is disposed in a matrix of an inert excipient insoluble in said fluid, said device being axially symmetrical, with said aperture being peripherally disposed so that the release surface of core which is exposed through said aperture is cylindrical or part of a cylinder in shape, whereby to allow substantially constant release of said active substance over at least part of the dissolution time.

2. A device as claimed in claim 1 wherein said active substance is uniformly disposed in said core and whereby on exposure of the device to said fluid medium a surface of said core is exposed to said fluid medium via said aperture and dissolution of said surface by said fluid medium causes a change in at least one dimension of the area of said surface whilst the surface area of said exposed surface remains substantially constant over at least 50% of the total dissolution time of said core, said device being axially symmetrical, with said aperture being peripherally disposed so that the exposed surface of active substance core is cylindrical or part of a cylinder in shape.

3. A device as claimed in claim 1 which is tablet-shaped.

4. A process for the preparation of a device as claimed in claim 1 wherein
   a) said covering material is blended with one or more excipients and compressed onto a pre-shaped core of active substance; or
   b) said covering material is blended with one or more excipients, granulated and compressed with granulated core material on a multi-layer press.

5. A device as claimed in claim 2 wherein the exposed surface of active substance core is substantially cylindrical or part of a cylinder in shape.

6. A device as claimed in claim 1 wherein said active substance is disposed in a matrix of an inert excipient insoluble in said fluid, said device being axially symmetrical, with said aperture being peripherally disposed so that the release surface of core which is exposed through said aperture is cylindrical or part of a cylinder in shape, whereby to allow substantially constant release of said active substance over at least part of the dissolution time.

7. A device as claimed in claim 6 wherein at least one of the core surfaces in contact with said covering is concave over at least 25% of the distance from the aperture to the centre of the core.

8. A device as claimed in claim 6 wherein said active substance is uniformly disposed throughout said inert matrix.

9. A device as claimed in claim 1 wherein said exposed surface of active substance core is accessible from two or more directions.

10. A device as claimed in claim 1 wherein said active substance core is toroidal in shape.

11. A device as claimed in claim 1 wherein said covering material comprises polyglycolide, poly (L-lactide), poly (DL-lactide), caprolactone, polyanhydrides, poly (orthoesters), poly (amino acids), ethyl cellulose, cellulose acetate phthalate, cellulose acetate, cellulose acetate butyrate, methacrylic acid copolymers, hydroxypropyl methylcellulose acetate phthalate, polyvinyl acetate phthalate, Eudragit RS, Eudragit RL, polypropylene, polyethylene, or mixtures thereof.

12. A device as claimed in claim 11 wherein said covering material comprises cellulose acetate, cellulose acetate butyrate, cellulose acetate phthalate, methacrylic acid copolymers, or mixtures thereof.

13. A device as claimed in claim 1 wherein said active substance is selected from muscle-relaxants, anti-Parkinson agents, analgesics, anti-inflammatory agents, muscle contractants, hormonal agents, contraceptives, diuretics, electrolytes, bronchodilators, antihypertensives, hypnotics, steroids, serotonin agonists or antagonists and $H_2$-antagonists.

14. A device as claimed in claim 13 wherein said active substance is salbutamol, labetalol, sumatriptan, ondansetron, 2,3,4,5-tetrahydro-5-methyl-2-[(5-methyl-1H-imidazol-4-yl)methyl]-1H-pyrido[4,3b]indol-1-one, (+)-1,2,3,9-tetrahydro-9-methyl-3-[(5-methyl-1H-imidazol-4-yl)methyl]-4H-carbozol-4-one, 6-fluoro 2,3,4,5-tetrahydro-5, methyl-2-[(5-methyl-1H-imidazol-4-yl)methyl]-1H-pyrido[4,3-b]indol-1-one, or a pharmaceutically acceptable salt or solvate thereof.

15. A device as claimed in claim 13 wherein said active substance is ranitidine or a pharmaceutically acceptable salt thereof.

* * * * *

UNITED STATES PATENT AND TRADEMARK OFFICE
CERTIFICATE OF CORRECTION

PATENT NO. : 5,342,627
DATED : August 30, 1994
INVENTOR(S) : Sham Kumar CHOPRA et al.

It is certified that error appears in the above-indentified patent and that said Letters Patent is hereby corrected as shown below:

On the Title page:

Item [56]

[56]　　　　　　　References Cited

U.S. Patent Documents

| | | | |
|---|---|---|---|
| 3,113,076 | 12/1963 | Jacobs | 167/82 |
| 3,851,648 | 12/1974 | Brooke | 128/260 |
| 4,792,448 | 12/1988 | Ranade | 424/438 |
| 4,803,076 | 02/1989 | Ranade | 424/438 |

Foreign Patent Documents

| | | |
|---|---|---|
| 0259219 | 03/1988 | Europe |
| 0259113 | 03/1988 | Europe |
| 1022171 | 03/1966 | Great Britain |

Signed and Sealed this

Twentieth Day of February, 1996

Attest:

BRUCE LEHMAN

*Attesting Officer*　　　*Commissioner of Patents and Trademarks*